United States Patent [19]

Haber

[11] Patent Number: 4,935,014
[45] Date of Patent: Jun. 19, 1990

[54] COMBINATION RETRACTABLE NEEDLE CANNUAL AND CANNUAL LOCK FOR A MEDICATION CARPULE

[75] Inventor: Terry M. Haber, El Toro, Calif.
[73] Assignee: Habley Medical Technology Corporation, Laguna Hills, Calif.
[21] Appl. No.: 248,910
[22] Filed: Sep. 26, 1988
[51] Int. Cl.⁵ .............................................. A61M 5/32
[52] U.S. Cl. .................................. 604/195; 604/110; 604/240
[58] Field of Search ............................... 604/195-198, 604/201-206, 240-243, 110

[56] References Cited
U.S. PATENT DOCUMENTS

| 3,063,450 | 11/1962 | Myerson et al. | 604/240 X |
| 3,150,661 | 9/1964 | Maki | 604/201 X |
| 4,808,169 | 2/1989 | Haber et al. | 604/110 X |
| 4,813,936 | 3/1989 | Schroeder | 604/195 |

Primary Examiner—Dalton L. Truluck
Attorney, Agent, or Firm—Morland C. Fischer

[57] ABSTRACT

A combination retractable needle cannula and cannula lock which is to be interfaced with a prefilled medication carpule at the cylinder of a conventional hypodermic syringe. The cannula lock includes a clamp having a pair of oppositely disposed jaws which are normally separated from one another so that the needle cannula can be releasably retained therebetween. In the pre-injection state, the jaws of the clamp are surrounded by and rotated towards one another by an expandable outer sleeve so as to retain the cannula in an axially extended position between the jaws for administering an injection. In the post-injection state, and after the contents of the carpule have been expulsed via the cannula, the clamp is displaced by the carpule outwardly of the sleeve, whereby the jaws of the clamp are free to rotate away from one another to release the cannula. The cannula may then be retracted within and completely surrounded by the empty carpule so that the cannula can be safely discarded after use while avoiding an accidental needle stick and the spread of a contagious, and possibly life threatening, disease.

10 Claims, 4 Drawing Sheets

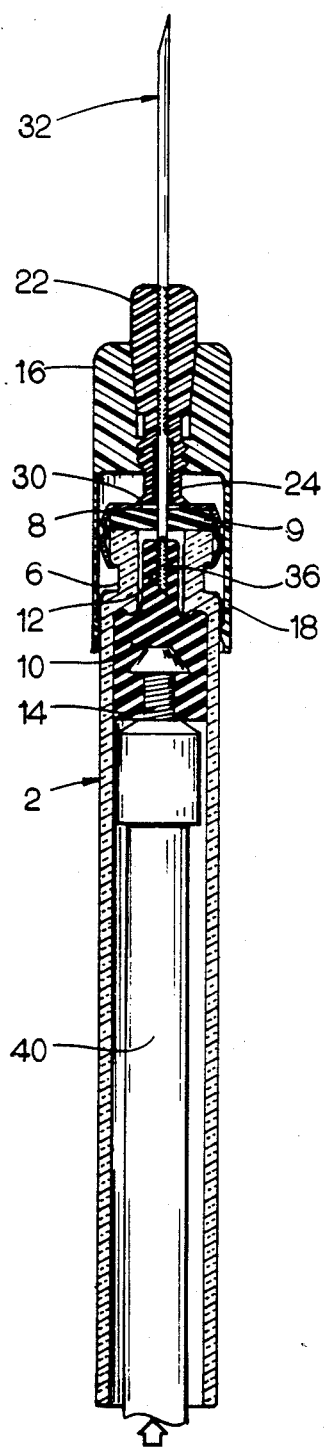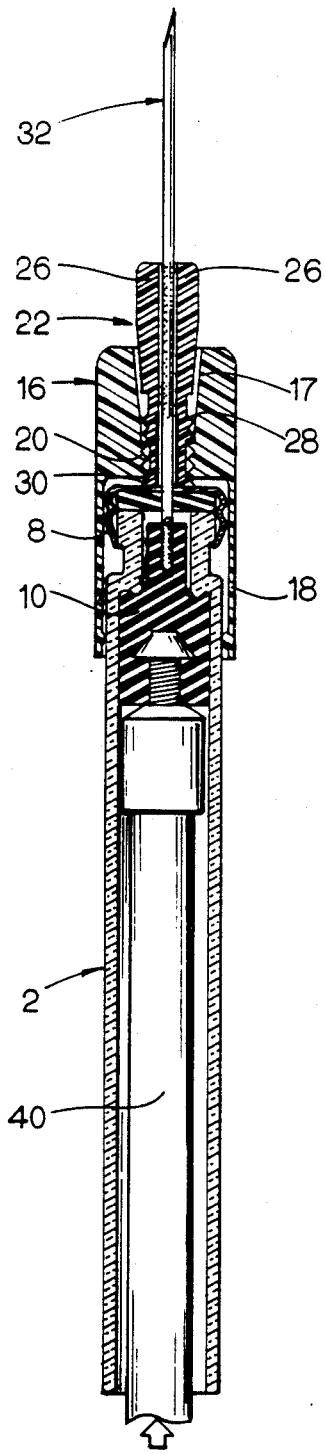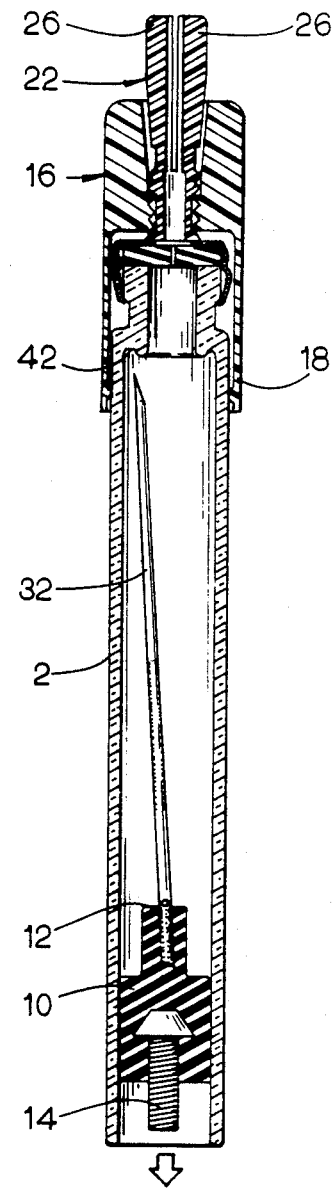

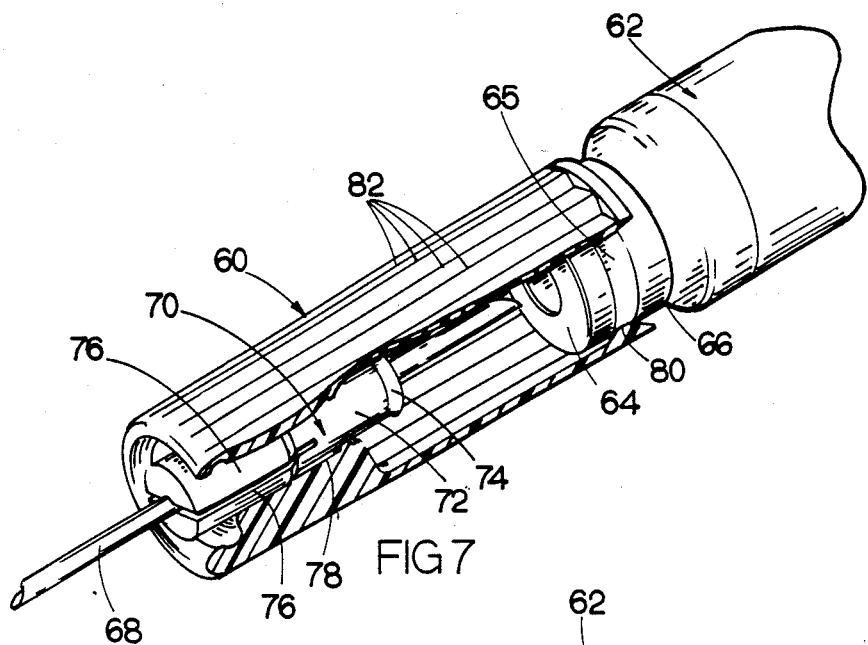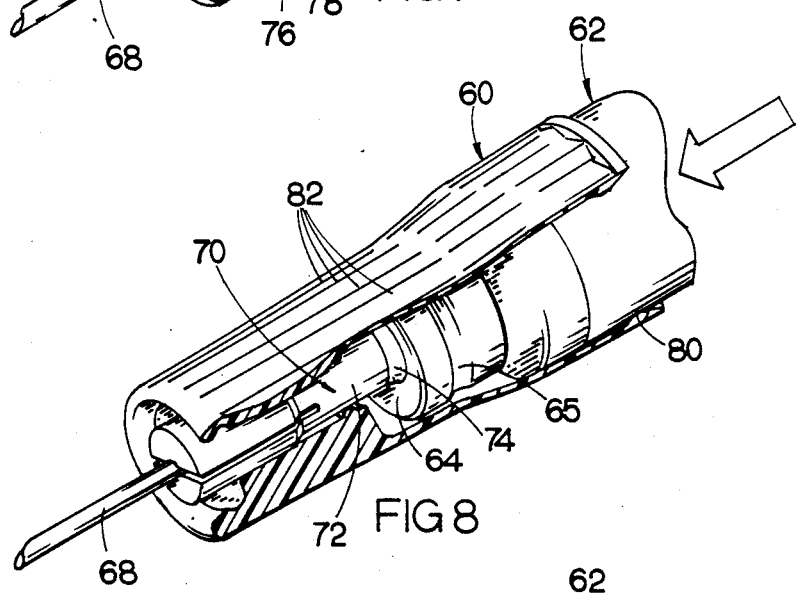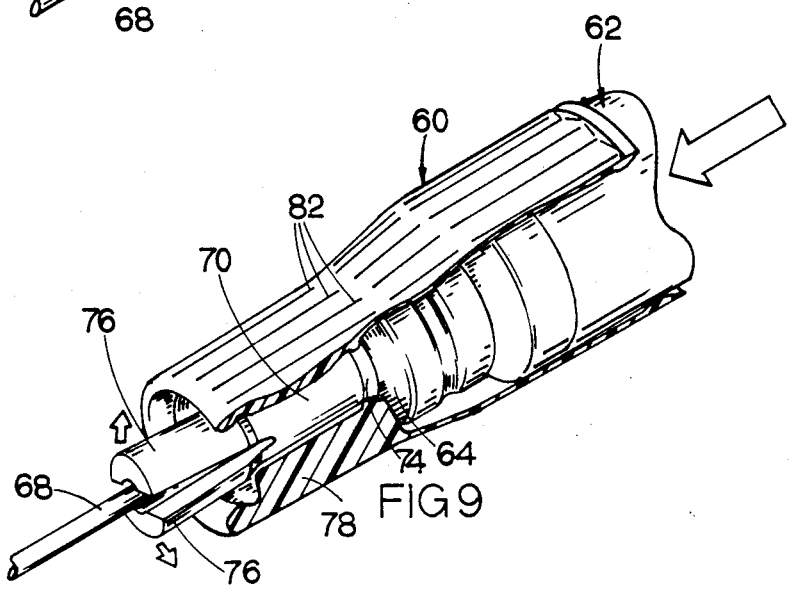

COMBINATION RETRACTABLE NEEDLE CANNUAL AND CANNUAL LOCK FOR A MEDICATION CARPULE

CROSS REFERENCES TO RELATED PATENT APPLICATIONS

This application is a continuation-in-part of U.S. patent application Ser. No. 211,366 filed Jun. 24, 1988.

BACKGROUND OF THE INVENTION

1. Field of the Invention

This invention relates to a combination needle cannula and cannula lock which is to be interfaced with a prefilled medication carpule at the interior of a hypodermic syringe so that the cannula can either be locked at an axially extended position for administering an injection or released from the axially extended position and retracted within and completely surrounded by said carpule, whereby the cannula may be safely discarded after use while avoiding an accidental needle stick and the possible spread of disease.

2. Prior Art

In U.S. Pat. No. 4,808,169 issued Feb. 28, 1989, which has been assigned to the assignee of the present invention, safety syringes are disclosed which have a prefilled medication carpule, a double ended hypodermic needle cannula, and means by which the needle cannula may be relocated from an axially extended position, at which the contents of the medication carpule are injected into a targeted tissue area, to a retracted position, at which the cannula is retracted within and completely surrounded by the carpule. Moreover, a pair of movable jaws was also disclosed for either retaining the cannula in the axially extended position or releasing the cannula for retraction into the carpule.

The present invention is directed to another embodiment of a safety syringe and, more particularly, to an efficient and reliable locking means by which a double ended needle cannula may be either retained in an axially extended position for administering an injection or released from the axially extended position to be retracted within and surrounded by an empty medication carpule. However, rather than the generally one-piece locking arrangements which are characteristic of the safety syringes of the above-mentioned co-pending patent application, the presently disclosed locking means is characterized by multiple components having particular dimensions, whereby to facilitate the manufacture and handling (i.e. during packaging) of the syringe and permit the cannula and locking means to be received by a conventional syringe cylinder without making modifications thereto. Nothing is known which is the same as or equivalent to the presently disclosed combination needle cannula and needle cannula locking means by which the position of a cannula relative to a medication carpule may be selectively and reliably controlled.

SUMMARY OF THE INVENTION

In general terms, a combination retractable needle cannula and needle cannula lock is disclosed to be interfaced with a prefilled medication carpule at the hollow cylinder of a hypodermic syringe. In the pre-injection state, a first end of the needle cannula extends outwardly from the distal end of the syringe cylinder and the second end projects into the cylinder to communicate with the carpule so that an injection may be administered. Locking means are provided to releasably retain the cannula in the outwardly extending position relative to the cylinder during the administration of the injection. The locking means includes a clamp which is disposed axially from the carpule during packaging. The clamp has a pair of normally spaced jaws that are movable towards one another and into engagement with the cannula for locking the cannula therebetween. The locking means also includes a generally cylindrical outer sleeve which is sized to surround the clamp and thereby move the jaws thereof towards one another and into engagement with the cannula. The outer sleeve may be provided with a plurality of longitudinally extending corrugations, whereby said sleeve is adapted to expand under a radially outward pressure. Thus, the expandable sleeve may be provided with a relatively narrow, non-obtrusive width so that the locking means may be better accommodated within the cylinder of a conventional syringe.

In the injection state, an axial force is applied to a piston stem, and an associated piston is moved axially and distally through the medication carpule to administer an injection. The second end of the needle cannula penetrates and is retained by the piston when the piston is advanced to the distal end of the carpule to expulse the fluid contents thereof via the cannula. The axial force being applied to the piston stem is transferred to the carpule by way of the piston, whereby to drive the carpule distally through the syringe cylinder and into contact with the needle retaining clamp. Accordingly, the clamp is displaced axially relative to the surrounding sleeve, such that the jaws of the clamp are now free to move away from one another and out of engagement with the cannula, whereby to permit the cannula to be removed from the jaws.

In the post-injection state, an axial pulling force is applied to the piston stem to relocate the piston proximally through the syringe cylinder. The needle cannula, which has been released by the clamp and retained by the piston, is, correspondingly, withdrawn from the clamp jaws and retracted into the empty medication carpule. Thus, the cannula is completely surrounded and shielded by the carpule, so that the cannula can be safely discarded after use while avoiding an accidental needle stick and the spread of a contagious, and possible life threatening, disease.

BRIEF DESCRIPTION OF THE DRAWINGS

FIGS. 3 and 4 show the combination needle cannula and cannula lock interacting with the medication carpule during the injection state when the fluid contents of said carpule are expulsed via the cannula;

FIG. 5 shows the combination needle cannula and cannula lock during the post-injection state when the cannula is retracted within and surrounded by the carpule;

FIG. 7 shows a combination needle cannula and cannula lock which forms an alternate embodiment of the present invention aligned with a medication carpule in the packaged, pre-injection state;

FIG. 8 shows the combination needle cannula and cannula lock of FIG. 7 interacting with the medication carpule in the injection state so that the fluid contents of said carpule can be expulsed via said cannula; and FIG. 9 shows the combination needle cannula and cannula lock of FIG. 7 in the post-injection state with said cannula conditioned to be retracted within and surrounded by the empty medication cartridge.

DESCRIPTION OF THE PREFERRED EMBODIMENT

Figure 1:
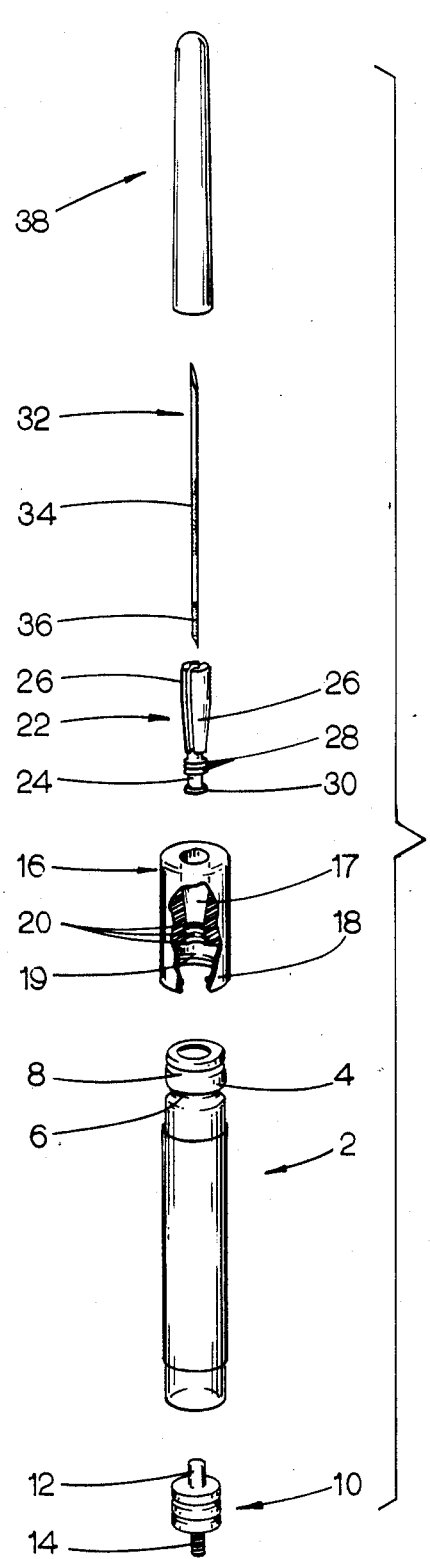
FIG. 1 is an exploded view of the combination retractable needle cannula and needle cannula lock which forms the present invention relative to a prefilled medication carpule.
Figure 6:
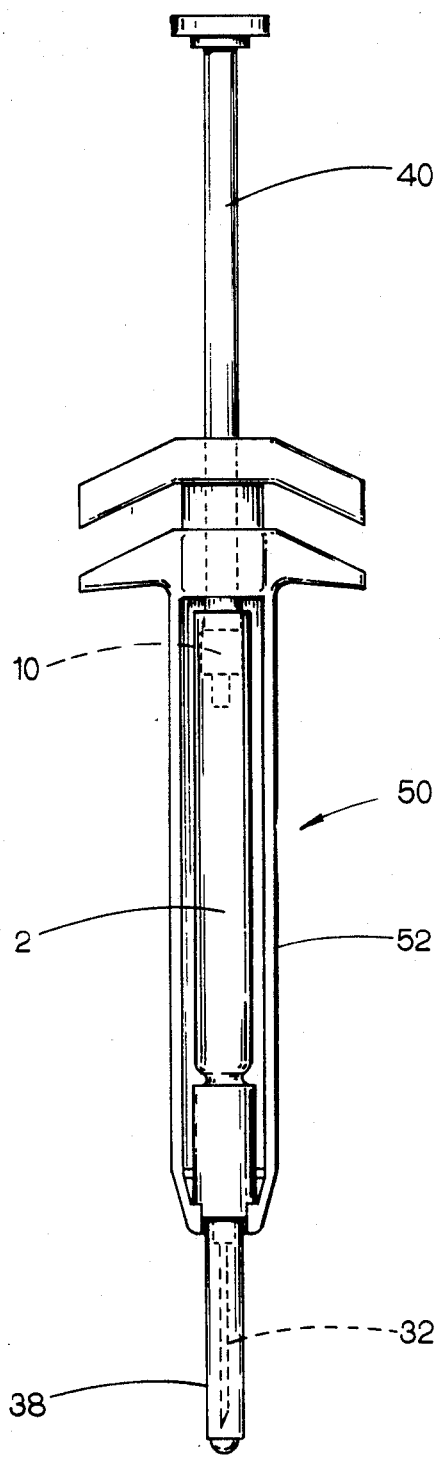
FIG. 6 is an example of a suitable syringe into which the combination needle cannula and cannula lock may be loaded and interfaced with a medication carpule to achieve the advantages of the present invention.

The combination retractable needle cannula and cannula lock which forms the present invention is best described while referring to the drawings, where FIG. 1 shows an exploded view of said combination in alignment with a disposable medication carpule, such as that designated by reference numeral 2. As illustrated in FIG. 6, the cannula, cannula lock, and medication carpule are adapted to be received within the hollow cylinder 52 of a commercially available syringe 50. Carpule 2 is of conventional design and includes a hollow, transparent body which is prefilled with a supply of fluid medication, or the like. Carpule 2 includes a head 4 and a cylindrical body which are coextensively joined together at a relatively narrow neck 6. A metallic end cap 8 covers a seal (designated 9 in FIG. 2) which extends across the carpule 2 to prevent contamination to and leakage of the fluid contents thereof.

A piston 10 is sized to be received in and slidable axially and reciprocally through the interior of medication carpule 2. Piston 10 is formed from a relatively dense, resilient (e.g. rubber) material and includes an integral nub 12 projecting from one end thereof. As will soon be disclosed, the purpose of nub 12 is to engage and retain one end of the retractable needle cannula when the piston 10 is moved distally through the carpule 2 for expulsing the fluid contents of said carpule via the cannula. A screw-threaded rod 14 is connected to the piston 10 so as to project outwardly from the end of piston 10 which is opposite the nub 12. Screw-threaded rod 14 is to be mated to a correspondingly screw-threaded piston stem (designated 40 in FIG. 6) so as to complete a piston assembly for controlling the movement of piston 10 through the interior of carpule 2.

Figure 2:
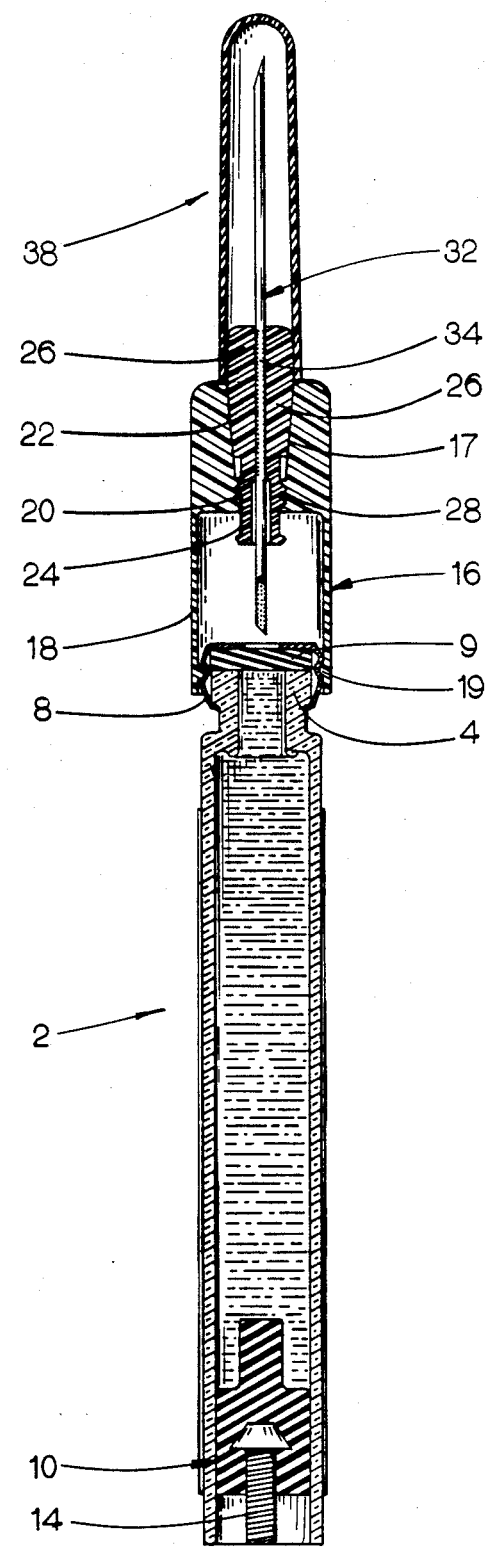
FIG. 2 shows the combination needle cannula and cannula lock of FIG. 1 aligned with the medication carpule in the packaged, pre-injection state.

A generally hollow, cylindrical sleeve 16 is provided having a relatively narrow, tapered bore 17 formed at the distal end thereof and a relatively wide body portion 18 formed at the proximal end which is sized to receive therewithin the head 4 of carpule 2. The sleeve 16 has a lower peripheral lip 19 extending around the interior of the proximal body portion 18 to enable sleeve 16 to be initially positioned with respect to carpule 2 during packaging (as best illustrated in FIG. 2). A series of alternating valleys and ridges or threads 20 extends around the periphery of the distal bore 17 of sleeve 16. As will be disclosed in greater detail hereinafter, the ridges 20 of sleeve 16 perform the important function of cooperating with complementary ridges of a soon to be described clamp or chuck 22 so as to either lock the needle cannula in an axially extended position for administering an injection or release the needle cannula to be retracted within and completely surrounded by the medication carpule 2.

More particularly, the aforementioned clamp or chuck 22 includes a hollow, generally cylindrical base 24 and a pair of parallel aligned jaws 26. The jaws 26 are normally spaced from one another and adapted to rotate relative to the base portion 24 so as to releasably receive and reliably retain a needle cannula 32 in the space therebetween. The jaws 26 have a tapered configuration to match the taper of the distal bore 17 of sleeve 16. A series of alternating valleys and ridges or threads 28 extend around the exterior periphery of base 24 to be mated to the ridges 20 of sleeve 16. An annular lip 30 is formed around the bottom of base 24.

Cannula 32 is a conventional double ended needle cannula of the type commonly associated with certain hypodermic syringes. However, cannula 32 includes a high friction, raised or textured medial surface 34 and another high friction, textured surface 36 located adjacent the proximal end thereof. A removable needle sheath 38 is also provided to surround cannula 32 during storage and handling to preserve the sterility of the cannula and prevent an accidental needle stick prior to use.

FIG. 2 of the drawings shows the assembled relationship of the retractable needle cannula 32 and the cannula lock therefor relative to the medication carpule 2 during packaging and storage. More particularly, the relatively wide proximal body portion 18 of sleeve 16 receives and engages the head 4 of medication carpule 2, such that the lower peripheral lip 19 of said body portion 18 is snap-fit within a dimple that is typically formed in the end cap 8. The needle cannula 32 is moved into the space between the opposing jaws 26 of the clamp 22 and the combination needle cannula 32 and clamp 22 is then located within the distal bore 17 of sleeve 16 so as to secure cannula 32 in an axially extending position for administering an injection. That is, the receipt of the tapered jaws 26 of clamp 22 within the similarly tapered bore 17 of sleeve 16 forces the jaws to rotate towards one another and into frictional engagement with the cannula 32 at the medially disposed textured surface 34 thereof, to oppose any axial displacement of said cannula relative to clamp 22. Moreover, the ridges/threads 28 at the base 24 of clamp 22 are snapped or screwed into engagement with the complementary ridges/threads 20 at the distal bore 17 of sleeve 16 to oppose any axial displacement of the clamp 22 relative to sleeve 16.

In the preinjection or packaged state shown in FIG. 2, the needle cannula 32 is axially aligned with but spaced from the carpule 2. The piston 10 is located at the proximal end of carpule 2 so as to be connected (at the threaded rod 14 of piston 10) to a piston stem (designated 40 in FIG. 6) for completing a piston assembly so that the fluid contents of carpule 2 can be expulsed during the administration of an injection. The needle sheath 38 is snapped into engagement with clamp 22 so as to surround and protect the outwardly projecting distal end of cannula 32 prior to the administration of an injection.

The operation of the combination needle cannula 32 and lock therefor during and after the administration of an injection is now described while referring to FIGS. 3-5 of the drawings. In the injection state of FIG. 3, the needle cannula 32, the cannula lock, and the medication carpule 2 of FIG. 2 are loaded into the cylinder of a suitable hypodermic syringe (designated 50 in FIG. 6) so that the distal end of the cannula extends outwardly from said cylinder. The carpule 2 is then advanced, by a health care worker, distally through the syringe cylinder and into the relatively wide proximal body portion 18 of sleeve 16. Accordingly, the inwardly extending proximal end of needle cannula 32 penetrates the end cap 8 and seal 9 of carpule 2 to communicate with the fluid contents of said carpule. Carpule 2 is continuously advanced through the proximal body portion 18 of sleeve 16 until the end cap 8 thereof is moved into contact with the annular lip 30 at the base 24 of clamp 22. The engagement of end cap 8 by lip 30 blocks the further distal displacement of the carpule 2 through the sleeve 16.

Next, the needle sheath (designated 38 in FIG. 6) is removed to expose the outwardly extending distal end of cannula 32. A screw-threaded piston stem 40 is connected to piston 10 at the screw-threaded rod 14 thereof. The cannula 32 is located at a targeted tissue area of the patient, and an axially and distally directed force is applied, by the health care worker, to piston stem 40. The distal force is transferred from piston stem 40 to the piston 10 to drive the piston through the medication carpule 2 and thereby expulse the fluid contents of said carpule via cannula 32.

At the conclusion of the injection, the piston 10 is located at the distal end of the medication carpule 2, such that the integral nub 12 of piston 10 is located within the neck 6 of said carpule, whereby the proximal end of cannula 32 penetrates the piston nub 12. The textured proximal surface 36 of cannula 32 enhances the retention of the cannula by the nub 12 and opposes the disconnection of the cannula from the nub.

After the injection has been administered and the needle cannula 32 received within and retained by the nub 12 of piston 10 at the distal end of carpule 2, the cannula 32 is released from the jaws 26 of clamp 22. That is to say, and referring to FIG. 4, the health care worker continues to apply an axially and distally directed force to the piston stem 40. The distally directed force is transferred from the piston stem to the empty medication carpule 2 via piston 10. More particularly, the piston 10 engages the distal end of carpule 2, so that any axially and distally directed force which is applied to said piston is also applied to the carpule. Accordingly, the carpule 2 is advanced distally through the interior of sleeve 16 until the end cap 8 of carpule 2 is located at the interface of the relatively wide body portion 18 with the relatively narrow distal bore 17.

Inasmuch as the clamp 22 is axially aligned with and engaged (i.e. at the annular lip 30 thereof) by the end cap 8 of carpule 2, the distal advancement of carpule 2 through sleeve 16 causes a corresponding distal advancement of clamp 22. That is, the axial force applied to clamp 22 (by way of piston stem 40, piston 10, and carpule 2) overcomes the interconnection of the ridges 28 of clamp 22 with the ridges 20 of sleeve 16. Hence, the clamp 22 is displaced axially relative to the sleeve 16 and, more particularly, distally relative to the distal bore 17 of said sleeve, whereby to permit the opposing jaws 26 of clamp 22 to rotate away from one another and out of engagement with the needle cannula 32. Therefore, the cannula 32 is now supported only by the piston 10 and is free to be removed from clamp 22.

FIG. 5 of the drawings illustrates the needle cannula 32 in the post-injection or retracted state, so that said cannula 32 is located within and completely surrounded by the empty medication carpule 2. More particularly, the health care worker applies an axial and proximal pulling force to the piston stem (designated 40 in FIG. 6) to relocate cannula 32 from the outwardly extended position, at which the injection was administered, to a relatively proximal position within carpule 2. The pulling force applied to the piston stem is transferred to the needle cannula 32 via the piston 10. Accordingly, the cannula 32 is withdrawn from the jaws 26 of clamp 22 and retracted within the carpule 2. By virtue of the foregoing, the cannula 32 is safely shielded by the carpule, whereby to avoid an accidental, and possibly life threatening, needle stick. Thereafter, the piston stem may be detached from the rod 14 of piston 10 and discarded. The carpule 2 may be popped out of the syringe cylinder and, likewise, discarded.

As an additional advantage of the present invention, the attachment of cannula 32 to the relatively dense, resilient material of the nub 12 of piston 10 will cause said cannula to be automatically canted when the cannula is retracted into the carpule 2. To this end, the carpule 2 may be formed with an optional, annular groove 42 that is positioned around the carpule so as to receive canted cannula 32 and thereby prevent the possible return of the cannula to the axially extended position (of FIG. 3) in the event that the piston stem (and the cannula connected thereto) is inadvertently moved axially and distally through the carpule 2.

FIG. 6 of the drawings illustrates a preferred example of a syringe 50 into which the assembly of FIG. 2 may be loaded in order to obtain the benefits of the presently disclosed invention. Syringe 50 includes a hollow cylinder 52 having an open side through which the medication carpule 2 is to be inserted and subsequently removed. Such a syringe 50 has particular application as a reusable dental syringe and is known commercially under the name CARPUJECT manufactured by Winthrop-Breon Corporation of New York. Reference may be made to copending U.S. patent application Ser. No. 181,204 filed Apr. 13, 1988 for a more detailed description of the operation of syringe 50 and, more particularly, the manner by which the piston stem 40 is connected to piston 10 and the means by which the medication carpule 2 is moved distally through cylinder 52 and into fluid communication with the needle cannula 32. However, it is to be expressly understood that the reusable dental syringe 50 illustrated in FIG. 6 is for purposes of example only, and, therefore, other suitable reusable and disposable syringe are also applicable herein.

FIGS. 7-9 of the drawings show an alternate embodiment of the present invention for a combination retractable needle cannula and cannula lock for a medication carpule. More particularly, the outer sleeve 16 which forms part of the cannula lock in FIGS. 1-6 is replaced by a modified outer sleeve 60. As will soon be described, the outer sleeve 60 is adapted to be interfaced with a disposable medication carpule 62 and received with said carpule at a hollow syringe cylinder. Medication carpule 62 is of conventional design and includes a transparent cylindrical body, an end cap 64, and a relatively narrow neck 66 disposed between the end cap and body. A piston (not shown) is slidable reciprocally through the interior of carpule 62 for the dual purpose of expulsing the contents of the carpule via a double ended hypodermic needle cannula 68 and for engaging a proximally oriented end of the cannula 68, such that the cannula may be retracted within and completely surrounded by an empty carpule.

Medication carpule 62 is axially aligned with and adapted to cooperate with a clamp or chuck 70 so as to either lock the needle cannula 68 in an axially extended position, at which an injection may be administered, or release the cannula 68 to be withdrawn in a proximal direction and shielded by the carpule 62. Referring particularly to the combination cannula and cannula lock in the as-packaged, pre-injection state of FIG. 7, the clamp 70 is shown including a hollow base portion 72 in which to receive and support the needle cannula 68 in spaced, concentric alignment with carpule 62. An annular lip 74 extends around the proximal end of the base portion 72. A pair of opposing, parallel aligned jaws 76 are hingedly attached to and extended distally from the base portion 72. The jaws 76 are normally spaced from one another and adapted to rotate relative to base portion 72 so as to releasably receive and reliably retain the needle cannula 68 in the space therebetween.

The outer sleeve 60 of the present embodiment is a generally hollow, cylindrical member that is of sufficient length to extend, in the pre-injection state of FIG. 7, between the jaws 76 of clamp 70 and the end cap 64 of medication carpule 62. A relatively thick, radially inward projecting contact surface 78 is formed around the periphery of sleeve 60 at the distal end thereof. Contact surface 78 is of suitable width to generate a sufficient compressive pressure for holding the jaws 76 of clamp 70 in a closed condition with the cannula 68 reliably retained therebetween. A relatively narrow, radially inward projecting ring 80 is formed around the periphery of sleeve 60 at the proximal end thereof. The ring 80 is of suitable size to be received within an annular groove 65 formed around the end cap 64 of carpule 62 to position outer sleeve 61 is the pre-injection state of FIG. 7, such that the proximally oriented end of cannula 68 is maintained in spaced, coaxial alignment with the carpule, the jaws 76 of clamp 70 are rotated to their closed configuration, and the radially inward extending contact surface 78 is spaced distally from the annular lip 74 at the base portion 72 of said clamp.

As an important detail of the present embodiment, the outside diameter of outer sleeve 60 is made slightly smaller than the maximum outside diameter of medication carpule 62. Moreover, the outer sleeve 60 is fabricated so as to be capable of expansion when subjected to a radially outward pressure (i.e. such as when the carpule 62 of relatively large diameter is moved into and through the interior of the sleeve 60 of relatively small diameter during the injection and post-injection states of FIGS. 8 and 9, respectively). So as to adapt the relatively narrow sleeve 60 to expand and thereby accommodate the relatively wide carpule 62 therewithin, the sleeve 60 is provided, around the periphery thereof, with a plurality of longitudinally extending corrugations 82 comprising successively alternating peaks and valleys. The foregoing corrugations 82 and the expansion capability provided thereby permit outer sleeve 60 and carpule 62 to be efficiently received in a conventional syringe cylinder (e.g. such as that designated 52 in FIG. 6) without requiring modification of the syringe.

The operation of the combination needle cannula 68 and lock therefor during the administration of an injection (FIG. 8) and afterwards (FIG. 9) is similar to that previously described when referring to FIGS. 3-5 of the drawings. Therefore, only a brief description will be provided of said combination in the injection and post-injection states. During the injection state, and referring particularly to FIG. 8, the needle cannula 68, the clamp 70, and the medication carpule 62 are all loaded into the cylinder of a suitable syringe (e.g. 50 in FIG. 6) so that the distal end of cannula 68 extends outwardly from the syringe cylinder. The carpule 62 is then manually and distally advanced (in the direction of the reference arrow) into the interior of outer sleeve 60, whereupon the groove 65 around end cap 64 is moved out of engagement with the ring 80 of sleeve 60. Accordingly, the proximal end of cannula 68 penetrates the end cap 64 of carpule 62 to communicate with the fluid contents thereof. Moreover, the corrugations 82 allow outer sleeve 60 to expand at the surface area thereof below which the carpule 62 has been advanced. Carpule 62 is continuously advanced through sleeve 60 until the end cap 64 is moved into contact with the clamp 70 at the annular lip 74 of base portion 72.

Next, the distal end of the cannula 68 is located at a targeted tissue area of the patient. A piston stem (such as that designated 40 in FIG. 6) is interfaced with the piston (such as that designated 10 in FIG. 6), and an axial and distally directed force is applied to the piston stem to drive the piston through the carpule 62 and thereby expulse the fluid contents thereof. At the conclusion of the injection, the piston will be located at the distal end of an empty carpule, whereby the proximal end of cannula 68, which penetrates the end cap 64 of said carpule, also penetrates the piston (best illustrated in FIG. 3).

In the post-injection state of FIG. 9, the needle cannula 68 is released from the jaws 76 of clamp 70. More particularly, the continued application of an axially and distally directed force to the piston stem is transferred to the empty medication carpule 62 to correspondingly advance the carpule distally (in the direction of the reference arrow) through the interior of outer sleeve 60 until the end cap 64 of carpule 62 is moved flush against the proximal end of the radially inward projecting contact surface 78 of sleeve 60. Inasmuch as the clamp 70 is aligned with and engaged by (i.e. at the annular lip 74 thereof) end cap 64, the distal advancement of carpule 62 through sleeve 60 also causes a distal advancement of the clamp. That is to say, the clamp 70 is displaced axially relative to sleeve 60 and, more particularly, distally relative to the radially inward projecting contact surface 78. Hence, the pressure formerly applied by contact surface 78 is removed, and the opposing jaws 76 of clamp 70 are permitted to rotate away from one another and out of engagement with the needle cannula 68.

The cannula 68, which is now supported only by the piston (in the manner illustrated in FIG. 4), is free to be withdrawn from the clamp 70 and retracted into the empty medication carpule 62. More particularly, by applying an axial and proximal pulling force to the piston stem (in the manner previously described while referring to FIG. 5), the cannula 68 is relocated from the outwardly extended position between the jaws 76 of clamp 70 at which the injection was administered, to a shielded position completely surrounded by the carpule. By virtue of the expansible characteristic of outer sleeve 60 as provided by the corrugations 82, the empty carpule 62 is anchored within the sleeve to prevent any proximal displacement of the clamp 70 relative to said sleeve and thereby facilitate the relocation of the cannula 68 into the carpule. Therefore, the carpule 62 can be removed from the syringe cylinder and discarded with the needle cannula safely and irretrievably located therewithin.

It will be apparent that while a preferred embodiment of the invention has been shown and described, various modifications and changes may be made without departing from the true spirit and scope of the invention. For example, although the clamp 22 or 70 has been described as moving axially and distally relative to the outer sleeve 16 or 60, it is within the scope of the claimed invention to otherwise axially displace the sleeve 16 or 60 relative to the clamp 22 or 60 so as to enable the jaws 26 or 76 of clamp 22 or 70 to move away from one another and, thereby, release the needle cannula 32 or 68 for retraction into the empty medication carpule 2 or 62.

Having thus set forth a preferred embodiment of the present invention, what is claimed is:

1. A hypodermic syringe including a generally hollow syringe cylinder for containing a supply of liquid to be injected into a patient and further comprising:
   a removable needle cannula to be connected to the syringe cylinder so that said cannula is in fluid communication with the liquid supply contained by said cylinder, said cannula having one end thereof extending outwardly from said cylinder for administering an injection of said liquid supply;
   a needle cannula lock coupled to the cannula to releasably engage and thereby retain said cannula at the outwardly extended position relative to said syringe cylinder;
   expansible sleeve means surrounding said cannula lock to hold said lock in releasable engagement with said cannula, said sleeve means adapted to expand in response to a radially outward pressure applied thereto; and
   means for moving said cannula lock axially relative to said sleeve so that said cannula lock releases its engagement of said cannula to permit said cannula to be removed from said lock.

2. The syringe recited in claim 1, further comprising a carpule containing said supply of fluid to be injected, said carpule being received by said syringe cylinder in axial alignment with said cannula lock, said needle cannula having a second end extending into said cylinder to penetrate said carpule and thereby communicate with the fluid supply thereof.

3. The syringe recited in claim 2, wherein the means for moving said cannula lock relative to said sleeve to release said cannula is said carpule, said carpule being movable axially through said syringe cylinder and into contact with said lock at the interior of said expansible sleeve, the movement of said carpule within said sleeve generating a radially outward pressure for causing said sleeve to expand.

4. The syringe recited in claim 3, wherein said expansible sleeve is provided with a plurality of corrugations which condition said sleeve for expansion when said carpule is moved therewithin.

5. The syringe recited in claim 4, wherein said corrugations extend longitudinally and in parallel alignment with one another along said expansible sleeve.

6. The syringe recited in claim 3, further comprising means for engaging the second end of said needle cannula and retracting said cannula out of said cannula lock and into said carpule after said carpule has moved said cannula lock relative to said expansible sleeve so that said cannula is released by said lock.

7. The syringe recited in claim 3, wherein the maximum outside diameter of said expansible sleeve in an unexpanded configuration is less than the maximum outside diameter of said carpule.

8. For receipt within the hollow cylinder of a hypodermic syringe, a combination needle cannula and cannula lock to be interfaced with a medication carpule located at the interior of said cylinder and containing a supply of fluid, said combination comprising:
   a needle cannula to be connected to the cylinder of said syringe so that one end of said cannula extends inwardly into said cylinder to penetrate said carpule and communicate with the fluid supply thereof, and the opposite end of said cannula extends outwardly from said cylinder to administer an injection;
   a needle cannula lock coupled to the cannula to releasably retain said cannula at the outwardly extending position relative to said syringe cylinder, said cannula lock including a pair of normally spaced jaws that are movable towards one another and into locking engagement with said cannula; and
   expansible sleeve means being aligned axially with said carpule and positioned to surround said cannula lock to thereby move said jaws thereof towards one another and into locking engagement with said cannula, said sleeve means provided with a plurality of corrugations so as to be expandable in response to a radially outward pressure applied thereto;
   said carpule movable axially through said syringe cylinder and into said expansible sleeve means for generating a radially outward pressure on said sleeve means to thereby cause said sleeve means to expand and for engaging and correspondingly moving said cannula lock axially relative to said sleeve means to permit said jaws to separate from one another and release their engagement of said cannula, whereby said cannula may be removed from said lock.

9. The combination recited in claim 8, wherein the maximum outside diameter of said expansible sleeve means in the unexpanded configuration is less than the maximum outside diameter of said carpule.

10. The combination recited in claim 8, wherein said expansible sleeve means comprises a generally hollow cylinder, said cylinder having a contact surface projecting radially inward therefrom to engage the jaws of said cannula lock for moving said jaws towards one another to lock said cannula therebetween.

* * * * *